(12) United States Patent
Grass et al.

(10) Patent No.: US 7,323,588 B2
(45) Date of Patent: Jan. 29, 2008

(54) ISONONYL BENZOATES AND THEIR USE

(75) Inventors: Michael Grass, Haltern am See (DE);
Juergen Koch, Haltern am See (DE)

(73) Assignee: OXENO Olefinchemie GmbH, Marl (DE)

( * ) Notice: Subject to any disclaimer, the term of this patent is extended or adjusted under 35 U.S.C. 154(b) by 378 days.

(21) Appl. No.: 10/418,103

(22) Filed: Apr. 18, 2003

(65) Prior Publication Data

US 2004/0015007 A1 Jan. 22, 2004

(30) Foreign Application Priority Data

Apr. 18, 2002 (DE) .............................. 102 17 186

(51) Int. Cl.
*C07C 69/76* (2006.01)
*C07C 231/00* (2006.01)
*C04B 9/02* (2006.01)
*C08L 9/10* (2006.01)
*B05D 5/10* (2006.01)
*B05D 5/00* (2006.01)

(52) U.S. Cl. .................. 560/103; 554/30; 106/14.13; 106/243; 427/208.8; 427/196

(58) Field of Classification Search .............. 560/103; 554/30; 106/14.13, 124.6, 243; 427/208.8, 427/196
See application file for complete search history.

(56) References Cited

U.S. PATENT DOCUMENTS 5,236,987 A 8/1993 Arendt 5,994,601 A 11/1999 Nierlich et al. ............. 585/329
2004/0015007 A1 1/2004 Grass et al.

FOREIGN PATENT DOCUMENTS

| CH | 274531 | 4/1951 |
|---|---|---|
| DE | 1 962 500 | 7/1970 |
| DE | 2 009 505 | 9/1971 |
| DE | 27 10 630 | 9/1978 |
| GB | 1 330 112 | 9/1973 |
| HU | 8012 | * 4/1974 |
| HU | 165522 | 12/1975 |
| JP | 2001-207002 | 7/2001 |
| WO | WO 97/39060 | 10/1997 |

OTHER PUBLICATIONS

Sugimoto et al, Mass spectrometry of fatty alcohol derivatives, 1983, Kanei Chuo Bunsekishoho, 24, p. 75-80.*
Rodinov et al, Alkyl benzoates, Metody Poluch, Khim. Reaktiv. Prep., 1970, No. 22, p. 7-10.*
T. B. Muravlyanskaya, et al., Database Caplus Online!, XP-002258318, AN74: 23306, 1 page, "Comparative Characteristics of Plasticizers", 1970.
Database Registry Online!, Chemical Abastracts Service, XP-002258319, 1 page, RN-91994-92-2, "Alcohols, C7-9-BRANCHED, C8-RICH".

(Continued)

*Primary Examiner*—Taylor Victor Oh
(74) *Attorney, Agent, or Firm*—Oblon, Spivak, McClelland, Maier & Neustadt, P.C.

(57) ABSTRACT

The invention relates to isomeric nonyl benzoates, processes for their preparation, mixtures of the same with alkyl phthalate, alkyl adipate, or alkyl cyclohexanedicarboxylate, and also to the use of these mixtures.

43 Claims, 1 Drawing Sheet

Gelling curves of plastisols 1-3

OTHER PUBLICATIONS

Database Registry Online!, Chemical Abstracts Service, XP-002258320, 1 page, RN-68526-83-0, "Alcohols, C7-9-ISO-, C8-RICH".

CRC Handbook of Chemistry and Physics, 76th Ed., p. 6-103.

U.S. Appl. No. 10/575,100, filed Apr. 10, 2006, Grass et al.

* cited by examiner

O.Z. 6004
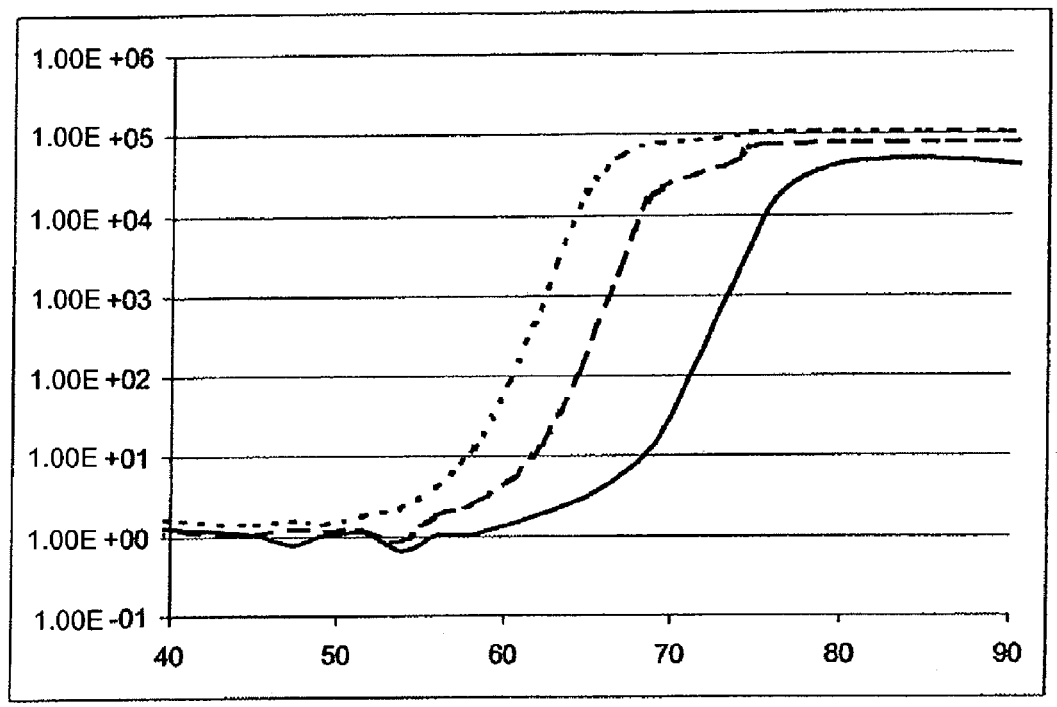
Fig 1: Gelling curves of plastisols 1-3

ISONONYL BENZOATES AND THEIR USE

BACKGROUND OF THE INVENTION

1. Field of the Invention

The present invention relates to isomeric nonyl benzoates, processes for their preparation, mixtures of the same with alkyl phthalates, alkyl adipates, or alkyl cyclohexanedicarboxylates, and also to the use of these mixtures.

2. Related Art of the Invention

Polyvinyl chloride (PVC) is one of the most commercially important polymers. It has a wide variety of uses both in the form of unplasticized PVC and in the form of plasticized PVC. To produce a plasticized PVC, plasticizers are added to the PVC. Examples of such plasticizers include phthalates such as di-2-ethylhexyl phthalate (DEHP), diisononyl phthalate (DINP), and diisodecyl phthalate (DIDP). As the chain length of the esters increases within such plasticizers, the solvation or gelation temperatures rise and the processing temperatures of the plasticized PVC rise.

The processing temperatures can be reduced by adding what are known as fast fusing plasticizers. Examples of such fast fusers are the short-chain phthalates, dibutyl phthalate (DBP), diisobutyl phthalate (DIBP), benzyl butyl phthalate (BBP), and diisoheptyl phthalate (DIHP). Moreover, dibenzoates, such as dipropylene glycol dibenzoates, or the like, may be used for the same purpose.

Due to their high solvating power, the presence of these fast fusers may lead to a marked rise in viscosity with time in PVC plastisols. In many cases, this has to be compensated by adding viscosity reducers which are often expensive.

A general demand during the preparation and processing of PVC plastisols is low viscosity and minimum gelation temperature. Another desirable feature of plastisol is a high shelf life which may be attributed to little increase in viscosity with time. High viscosity may be disadvantageous during processing of the plastisol in machinery. Further, an excessively high gelation temperature may lead to discoloration due to thermal stress.

There are only a few known plasticizers that provide a significant lowering of the gelation temperature in formulations and simultaneously maintain the viscosity of the plastisol at a low level, much less after storage for a period of some days. 2-Ethylhexyl benzoate has recently been proposed as a product which could provide these benefits [Bohnert, Stanhope, J. Vinyl Addit. Technol. (2000), 6(3), 146-149]. However, this compound has comparatively high vapor pressure, which leads to unacceptable losses of this compound during processing.

DE 19 62 500 discloses the use of a mixture of relatively long-chain esters of benzoic and phthalic acid for preparing plastisols. 3,5,5-Trimethylhexanol is preferably used for preparing the benzoates. No precise information is given concerning the phthalic diesters that may be used.

The use of phthalates whose ester groups have from 1 to 8 carbon atoms is more and more restricted due to toxicological reasons. Further, esters having relatively long alkyl side chains are classified as less toxicologically hazardous, but have poorer processing properties.

SUMMARY OF THE INVENTION

A first object of the present invention is therefore to improve the gelling properties, the low-temperature flexibility and shelf life of the abovementioned plasticizer systems in PVC.

A second object of the present invention is therefore to find novel plasticizers for plastics, e.g. for PVC, which may be based on low-cost raw materials and may have equivalent or improved plasticizer properties, such as improved low-temperature-flexibilizing power and lower volatility, while their plastisols may have the lower viscosity level.

The above objects are accomplished, in part, by a third object of the present invention which is related to isononyl benzoates. These isononyl benzoates may be used alone or in a mixture with phthalic esters and/or with dialkyl adipates, and/or with cyclohexyldicarboxylic esters.

A fourth object of the present invention is therefore to provide mixtures of isomeric isononyl benzoates. The nonyl alcohols may be obtained by saponifying the isomeric isononyl benzoates containing less than 10 mol % of 3,5,5-trimethylhexanol.

A fifth object of the present invention is therefore to provide processes for preparing mixtures of isomeric isononyl benzoates by esterifying benzoic acid with nonyl alcohols which contain less than 10 mol % of 3,5,5-trimethylhexanol.

A sixth object of the present invention is therefore to provide processes for preparing mixtures of isomeric isononyl benzoates by transesterifying one or more alkyl benzoates whose alkyl radicals contain from 1 to 8 carbon atoms with nonyl alcohols which comprise less than 10 mol % of 3,5,5-trimethylhexanol.

DETAILED DESCRIPTION OF THE INVENTION

The saponification of benzoic esters or of other esters mentioned below may be carried out by conventional methods via reaction with alkaline media (see, for example, Ullmann's Enzyklopädie der Technischen Chemie [Ullmann's Encyclopedia of Industrial Chemistry], 5th Edn. A 10, pp. 254-260).

The nonyl alcohols used to prepare the mixtures of the invention are generally isomer mixtures and are often termed isononanols. The mixtures of the invention or the nonyl alcohols used in the process of the invention have high linearity which is characterized by a proportion of from 0 to 10 mol %, preferably from 0 to 5 mol %, particularly preferably from 0 to 2 mol %, of 3,5,5-trimethylhexanol. The proportion of 3,5,5-trimethylhexanol may be 1, 2, 3, 4, 5, 6, 7, 8, and 9 mol %, including all ranges and subranges therebetween. These data are applicable to all of the mixtures mentioned below. Mixtures of this type are commercially available and known as CAS numbers 27458-94-2, 68515-81-1, 68527-05-9, or 68526-84-1.

"CAS Number" means Chemical Abstracts Registry Number. The isomer distributions of the nonyl radicals may be determined using the usual test methods familiar to the skilled worker. Examples of such test, methods may be NMR spectroscopy, GC, or GC/MS spectroscopy.

The nonyl benzoates of the present invention may be used as viscosity reducers and fast fusing plasticizers. When compared with known systems in the modification of plastics (polymers) such as PVC, these nonyl benzoates very advantageously combine low volatility, good gelling capability, good low-temperature flexibilization, and little rise in viscosity in plastisols.

In one version of a process of the present invention, one or more alkyl benzoates are transesterified. Examples of such alkyl benzoates may be methyl benzoate, ethyl benzoate, propyl benzoate, isobutyl benzoate, amyl benzoate, and/or butyl benzoate.

For preparing the isononyl benzoates of the present invention, as well as the cyclohexanedicarboxylic esters and/or the nonyl adipates and/or nonyl phthalates used, it is preferable to use industrial nonanol mixtures. Nonanol mixtures are also known as mixtures of isomeric alcohols. Hereinafter the above-mentioned nonanol mixtures and mixtures of isomeric alcohols are termed isononanol or isononanol mixture.

The isomer distribution in these mixtures may be determined by the nature of the preparation process of the nonyl alcohol, e.g. isononanol, used.

Isononanol may be prepared by hydroformylating octenes. Octenes may be produced in various ways. Industrial C4 streams are the raw material that may be generally used for this purpose. C4 streams initially contain all isomeric forms of C4 olefins, as well as the saturated butanes. Further, C4 streams may also contain contaminants. Examples of such contaminants may include C3 and C5 olefins, as well as acetylenic compounds. Oligomerization of the C4 stream containing olefin mixture may produce isomeric octene mixtures alongside higher oligomers, such as C12 and C16 olefin mixtures.

These octene mixtures may be hydroformylated to produce the corresponding aldehydes and then may be hydrogenated to produce the alcohol.

The composition industrial nonanol mixtures contains an isomer distribution which depends on the starting material and on the oligomerization and hydroformylation processes from which it is produced. Any of these mixtures may be used to prepare the esters of the invention. Preferred nonanol mixtures are those that may be obtained by hydroformylating C8 olefin mixtures obtained by oligomerizing substantively linear butenes in the presence of nickel supported catalysts, e.g. the OCTOL process, in the presence of unmodified cobalt compounds, followed by hydrogenation of the catalyst-depleted hydroformylation mixture. The proportion of isobutene in the starting material, based on total butene content, may be less than 5% by weight, preferably less than 3% by weight, particularly preferably less than 1% by weight. The proportion of isobutene in the starting material, based on the total butene content, may also be 4, 3, 2, 1, and 0% by weight, including all ranges and subranges therebetween.

The result of the above-mentioned process is that the proportion of more highly branched nonanol isomers, including, inter alia, 3,5,5-trimethylhexanol, which is proven less advantageously, is markedly suppressed. As a result, mixtures of the invention contain less than 10% by weight, preferably less than 5% by weight, particularly preferably less than 3% by weight, in particular less than 1% by weight, of esters of 3,5,5-trimethylhexanol. The amount of esters of 3,5,5-trimethylhexanol may be 9, 8, 7, 6, 5, 4, 3, 2, and 1, including ranges and subranges therebetween. These data are based on the alcohol mixtures which result from saponification of the ester mixtures of the invention.

The present invention also provides alkyl benzoate mixtures from which the alcohol mixture obtained by saponification corresponds to the alcohols with CAS numbers 68551-09-7, 91994-92-2, 68526-83-0, 66455-17-2, 68551-08-6, 85631-14-7, or 97552-90-4. These are alcohol mixtures which contain the above-mentioned isononyl, as well as alcohols having from 7 to 15 carbon atoms (in accordance with CAS definition).

The present invention also provides mixtures of the isononyl benzoates, preferably the above-mentioned isononyl benzoates with dialkyl phthalates such as diisononyl phthalate, or with dialkyl adipates such as diisononyl adipates, or with alkyl cyclohexanedicarboxylates, such as diisononyl cyclohexanedicarboxylates.

The mixtures of the present invention may be defined as follows:

a) Mixtures containing from 1 to 99% by weight of isomeric isononyl benzoates, where the nonyl alcohols obtained by saponifying these benzoates contain less than 10 mol % of 3,5,5-trimethylhexanol, and contain from 1 to 99% by weight of dialkyl phthalates whose alkyl radicals contain from 4 to 13 carbon atoms. The amount by weight of isomeric isononyl benzoates may be 2, 5, 10, 15, 20, 25, 30, 35, 40, 45, 50, 55, 60, 65, 70, 75, 80, 85, 90, and 95%, including all ranges and subranges therebetween. The amount of 3,5,5-trimethylhexanol may be 9, 8, 7, 6, 5, 4, 3, 2, and 1 mol %, including all ranges and subranges therebetween. The amount by weight of dialkyl phthalates may be 2, 5, 10, 15, 20, 25, 30, 35, 40, 45, 50, 55, 60, 65, 70, 75, 80, 85, 90, and 95%, including all ranges and subranges therebetween. The number of carbon atoms contained by the alkyl radical of dialkyl phthalates may be 5, 6, 7, 8, 9, 10, 11, and 12, including all ranges and subranges therebetween.

Preferred phthalic esters are diIsononyl phthalates. In particular, the isononanols obtained by saponifying the diisononyl phthalates contain less than 10 mol % of 3,5,5-trimethylhexanol. The amount of 3,5,5-trimethylhexanol may be 9, 8, 7, 6, 5, 4, 3, 2, and 1 mol %, including all ranges and subranges therebetween.

b) Mixtures comprising from 1 to 99% by weight of isomeric isononyl benzoates, where the nonyl alcohols obtained by saponifying these benzoates contain less than 10 mol % of 3,5,5-trimethylhexanol, and contain from 1 to 99% by weight of alkyl adipates whose alkyl radicals contain from 4 to 13 carbon atoms. The amount by weight of isomeric isononyl benzoates may be 2, 5, 10, 15, 20, 25, 30, 35, 40, 45, 50, 55, 60, 65, 70, 75, 80, 85, 90, and 95%, including all ranges and subranges therebetween. The amount of 3,5,5-trimethylhexanol may be 9, 8, 7, 6, 5, 4, 3, 2, and 1 mol %, including all ranges and subranges therebetween. The amount by weight of alkyl adipates may be 2, 5, 10, 15, 20, 25, 30, 35, 40, 45, 50, 55, 60, 65, 70, 75, 80, 85, 90, and 95%, including all ranges and subranges therebetween. The number of carbon atoms contained by the alkyl radical of alkyl adipates may be 5, 6, 7, 8, 9, 10, 11, and 12, including all ranges and subranges therebetween.

A preferred alkyl adipate is diisononyl adipate. It is particularly preferable that the isononyls obtained by saponifying the diisononyl adipates contain less than 10 mol % of 3,5,5-trimethylhexanol. The amount of 3,5,5-trimethylhexanol may be 9, 8, 7, 6, 5, 4, 3, 2, and 1 mol %, including all ranges and subranges therebetween.

c) Mixtures comprising from 1 to 99% by weight of isomeric isononyl benzoates, where the nonyl alcohols obtained by saponifying these benzoates contain less than 10 mol % of 3,5,5-trimethylhexanol, and containing from 1 to 99% by weight of alkyl cyclohexanedicarboxylate whose alkyl radicals contain from 4 to 13 carbon atoms. The amount by weight of isomeric isononyl benzoates maybe 2, 5, 10, 15, 20, 25, 30, 35, 40, 45, 50, 55, 60, 65, 70, 75, 80, 85, 90, and 95%, including all ranges and subranges therebetween. The amount of 3,5,5-trimethylhexanol may be 9, 8, 7, 6, 5, 4, 3, 2, and 1 mol %, including all ranges and subranges therebetween. The amount by weight of alkyl cyclohexanedicarboxylate may be 2, 5, 10, 15, 20, 25, 30, 35, 40, 45, 50, 55, 60, 65, 70, 75, 80, 85, 90, and 95%, including all ranges and subranges therebetween.

The number of carbon atoms contained by the alkyl radical of alkyl cyclohexanedicarboxylate may be 5, 6, 7, 8, 9, 10, 11, and 12, including all ranges and subranges therebetween.

A preferred dialkyl cyclohexanedicarboxylate is diisononyl cyclohexanedicarboxylate. It is particularly preferable that the isononanols obtained by saponifying the isononyl cyclohexanedicarboxylates contain less than 10 mol % of 3,5,5-trimethylhexanol. Among the cyclohexanedicarboxylic esters, preference is given to those having 1,2-positioned carboxy groups. The amount of 3,5,5-trimethylhexanol may be 9, 8, 7, 6, 5, 4, 3, 2, and 1 mol %, including all ranges and subranges therebetween.

In each of the above-mentioned mixtures, the proportions of the esters mentioned give 100% in total.

Mixtures of the invention are defined via the composition of the esters mentioned, not via the nature or sequence of preparation of the mixtures. Mixtures of the present invention are also present when the esters mentioned are mixed in the ratio mentioned, simultaneously or in succession, with another substance, such as plastics, (e.g. PVC).

An autocatalytic or catalytic method may be used to esterify the benzoic acid, phthalic acid or phthalic anhydride, and/or adipic acid and/or cyclohexanedicarboxylic acid or its anhydride with an isomerically pure nonanol or with an isononanol mixture to produce the corresponding esters. Such methods may utilize Bronsted or Lewis acids. Quite irrespective of the nature of the catalysis selected, the result is always a temperature-dependent equilibrium between the starting materials (e.g. acid and alcohol) and the products (e.g. ester and water). In order to shift the equilibrium in favor of the ester, an entrainer may be utilized; thereby removing the water of the reaction from the mixture. Since the alcohol mixtures used for the esterification process have lower boiling points than the benzoic acid and its esters and are not fully miscible with water, they are often used as an entrainer which can be returned to the process after water-separation.

The alcohol or, respectively, isomeric alcohol mixture used to form the ester and simultaneously used as an entrainer is also used in excess, this preferably being from 5 to 50%, in particular from 10 to 30%, of the amount needed to form the ester. The excess amount of alcohol or isomeric alcohol mixture used may be 10, 15, 20, 25, 30, 35, 40, and 45% of the amount needed to form the ester.

Examples of esterification catalysts which may be used are acids and metals and their compounds. More specifically, such acids include, but are not limited to, sulfuric acid, methane sulfonic acid, p-toluenesulfonic acid. Further, examples of metals and their compounds suitable are tin, titanium, and zirconium. These metals may be used in the form of finely divided metals. Advantageously, these metal may be in the form of their salts, oxides, or soluble organic compounds. Unlike protonic acids, the metal catalysts are high-temperature catalysts whose full activity is often not achieved until temperatures reach above 180° C. However, their use is preferred since the level of formation of by-products such as olefins from the alcohol used is lower when compared to protonic catalysis. Preferred examples of metal catalysts are tin powder, stannous oxide, stannous oxalate, titanium esters such as tetraisopropyl orthotitanate or tetrabutyl orthotitanate, and zirconium esters such as tetrabutyl zirconate.

The concentration of catalyst depends on the nature of the catalyst. In the case of the titanium compounds preferred, it is from 0.005 to 1.0% by weight, based on the reaction mixture, in particular from 0.01 to 0.5% by weight, very particularly from 0.01 to 0.1% by weight. The concentration of titanium compound is 0.01, 0.02, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9. and 0.95% by weight, including all ranges and subranges therebetween.

When titanium catalysts are used, the reaction temperature is from 160 to 270° C., preferably from 180 to 250° C. The reaction temperature may be 170, 180, 190, 200, 210, 220, 230, 240, 250, and 260° C. The ideal temperature depends on the starting materials, the progress of the reaction, and the concentration of catalyst. They may readily be determined by trials for each individual case. Higher temperatures increase the reaction rates and favor side reactions, such as elimination of water from alcohols or formation of colored by-products. For removal of the water of the reaction, it is advantageous that the alcohol can be distilled off from the reaction mixture. The desired temperature or the desired temperature range may be set via the pressure in the reaction vessel. For this reason, the reaction is carried out at superatmospheric pressure in the case of low-boiling alcohols utilized and at subatmospheric pressure in the case of relatively high-boiling alcohols utilized. For example, operations for the reaction of benzoic acid with a mixture of isomeric nonanols are carried out in a range of temperature from 170 to 250° C. in the range of pressures from 1 bar to 10 mbar.

Some or all of the liquid to be returned to the reaction may be composed of alcohol obtained by work-up of the azeotropic distillate. It is also possible to carry out the work-up at a later juncture, and to replace some or all of the amount of liquid removed by fresh alcohol, i.e. alcohol provided in a feed vessel.

The crude ester mixtures, which comprise by-products as well as the ester, alcohol, and catalyst or products derived from the catalyst, are worked up by processes known per se. This work-up encompasses the following steps: removal of the excess alcohol and, where appropriate, low-boilers, neutralization of the acids present, and optional steam distillation, conversion of the catalyst into a residue which is easy to filter, removal of the solids, and, where appropriate, drying. The sequence of these steps may differ, depending on the work-up process used.

The nonyl ester or the mixture of the nonyl esters may be removed from the reaction mixture by distillation, after neutralization of the mixture, if appropriate.

As an alternative, the nonyl benzoates of the invention may be obtained by transesterifying a benzoic ester with nonanol or with an isononanol mixture. The starting materials used comprise benzoic esters whose alkyl radicals bonded to the oxygen atom of the ester group contain from 1 to 8 carbon atoms. The carbon atoms of the ester group may be 2, 3, 4, 5, 6, and 7, including all ranges and subranges therebetween. These radicals may be aliphatic, straight-chain or branched, alicyclic, or aromatic. One or more methylene groups in these alkyl radicals may have been substituted by oxygen. It is advantageous that the alcohols on which the starting ester is based have lower boiling points than the isononanol mixture or nonanol used. Methyl benzoate is a preferred starting material.

The transesterification is carried out catalytically, for example using Bronsted or Lewis acids, or using bases. Quite irrespective of the catalyst used, the result is always a temperature-dependent equilibrium between the solid material (e.g. alkyl benzoate and isononanol mixture or nonanol) and the products (e.g. nonyl ester or nonyl ester mixture and liberated alcohol). In order to shift the equilibrium in favor of the nonyl ester or of the isononyl ester mixture, the alcohol produced from the starting ester is distilled off from the reaction mixture. Here, too, it is advantageous to use an excess of the isononanol mixture or nonanol.

Transesterification catalysts which may be used are acids, such as sulfuric acid, methanesulfonic acid, or p-toluene sulfonic acid, or metals or their compounds. Further examples of those suitable are tin, titanium, and zirconium which may be used in the form of finely divided metals, or more preferably in the form of their salts, oxides, or soluble organic compounds. Unlike protonic acids, the metal catalysts are high-temperature catalysts whose full activity is often not achieved until temperatures reach above 180° C. However, their use is preferred since the level of formation of by-products, such as olefins from the alcohol used, is lower when compared to protonic catalysis. Examples of suitable metal catalysts are tin powder, stannous oxide, stannous oxalate, titanium esters such as tetraisopropyl orthotitanate or tetrabutyl orthotitanate, and zirconium esters such as tetrabutyl zirconate.

Basic catalysts, such as oxides, hydroxides, hydrogen carbonates, carbonates, or alkoxides of alkali metals or of alkaline earth metals may be used. Among these catalysts, preference is given to use of alkoxides such as sodium methoxide. It is also possible to prepare alkoxides in situ from an alkali metal and an isonanol mixture or a nonanol.

The concentration of catalyst depends on the nature of the catalyst. It is usually from 0.005 to 1.0% by weight, based on the reaction mixture. The concentration of catalyst is 0.01, 0.02, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9. and 0.95% by weight, including all ranges and subranges therebetween.

The reaction temperature for transesterification are usually from 100 to 220° C. The reaction temperatures may also be 110, 120, 130, 140, 150, 160, 170, 180, 190, 200, and 210° C., including all ranges and subranges therebetween. It has to be at least high enough to permit the alcohol produced from the starting ester to be distilled off from the reaction mixture at the prevailing pressure, mostly atmospheric pressure.

The work-up of the transesterification mixtures may be precisely as described for the esterification mixtures.

The mixtures of the invention, alone or in combination with other plasticizers, may be incorporated in plastics (polymers). Preferred plastics are PVC, PVB, homo- and copolymers based on ethylene, on propylene, on butadiene, on vinyl acetate, on glycidyl acrylate, on glycidyl methacrylate, or on acrylates having, bonded to the oxygen atom of the ester group, alkyl radicals of branched or unbranched alcohols having from 1 to 10 carbon atoms. The number of carbon atoms may be 2, 3, 4, 5, 6, 7, 8, and 9, including all ranges and subranges therebetween. Other preferred plastics are styrene, acrylonitrile, and homo- or copolymers of cyclic olefins.

Examples which may be mentioned of representatives of the above groups are the following plastics:

polyacrylates having identical or different alkyl radicals having from 4 to 10 carbon atoms bonded to the oxygen atom of the ester group, in particular having the n-butyl, n-hexyl, n-octyl, isononyl, or 2-ethylhexyl radical, polymethacrylate, polymethyl methacrylate, methyl acrylate-butyl acrylate copolymers, methyl methacrylate-butyl methacrylate copolymers, ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, methyl methacrylate-styrene-butadiene copolymers, and/or nitrolocellulose. The number of carbon atoms may be 5, 6, 7, 8, and 9, including all ranges and subranges therebetween.

PVC grades which may be used are suspension, bulk, microsuspension, and preferably emulsion PVC. Besides the esters described of cyclohexanedicarboxylic acid, phthalic acid, adipic acid, and benzoic acid, as well as other plasticizers, there may also be numerous other components known to the skilled worker added to the mixing specification. Examples of these are fillers, pigments, stabilizers, lubricants, blowing agents, kickers, antioxidants, biocides, etc.

The mixtures of the invention are preferably used for producing plastisols, in particular PVC plastisols, with particularly advantageous processing properties. These plastisols may be used in numerous products, such as synthetic leathers, flooring, or wallpapers, etc. Among these applications, particular preference is given to use in cushion vinyl (CV) flooring, and in particular here in the outer layer, where a further improvement is brought about in stain resistance. Use of the mixtures of the invention as a constituent in a mixing specification can give plastisols with low viscosity and increased storage stability together with accelerated gelling and improved low-temperature flexibilization.

It is also possible for the nonylbenzoates or the above-mentioned mixtures of the invention with phthalates, with adipates, and/or with cyclohexanedicarboxylates, to be used as flexibilizers in coatings, paints, and inks, or components of adhesives.

EXAMPLES

The examples below are intended to illustrate the invention without restricting the scope of application arising from the Description and the claims.

Example 1

Preparation of Isononyl Benzoate 976 g of benzoic acid (8 mol), 1728 g of isononanol from OXENO Olefinchemie GmbH (12 mol), and 0.59 g of butyl titanate (0.06%, based on the amount of acid) are weighed into a four liter distillation flask on top of which a water separator and reflux condenser have been attached, and which has a sampling port and thermometer, and are heated to boiling under nitrogen. The water of reaction produced during the esterification process was removed sequentially. Once the acid value fell below 0.1 mg KOH/g (after about 3 hours), the mixture was first cooled below 60° C., and a 20 cm multifill column was placed on the apparatus. The pressure was then reduced to 2 mbar, and excess alcohol was first distilled off (about 120° C.). After removal of an intermediate fraction at up to 140° C. it was possible to distill over the isononyl benzoate within a range of 142 to 147° C. (at 2 mbar) measured at the head of the column. Purity >99.7% was determined by gas chromatography.

The dynamic viscosity of the product at 20° C. was 8.4 mpa*s.

Example 2

Preparation of 2-ethylhexyl Benzoate (Comparative Example)

Using a method similar to the procedure carried out in Example 1, 12 mol of 2-ethylhexanol were reacted with 8 mol of benzoic acid and tetrabutyl titanate. Distillation gave 2-ethylhexyl benzoate with purity of 99.7% determined by gas chromatography.

The dynamic viscosity of the product at 20° C. was 6.8 mpa*s.

Example 3

Preparation of 3,5,5-trimethylhexyl Benzoate (Comparative Example)

1000 g of 2,4,4-trimethyl-1-pentene (diisobutene) from Oxeno (may be prepared as in DE 10106593.0, for example) were hydroformylated in a 2 l autoclave at 135° C. under 270 bar of synthesis gas pressure for 3 hours in the presence of an unmodified rhodium catalyst. The active catalyst was generated in situ from rhodium nonanoate (24.8% by weight of Rh). Rhodium concentration based on diisobutene was set at 20 ppm.

After 3 hours the reaction was terminated and the autoclave was cooled to 20° C.

The reaction discharge comprises 93.5% by weight of 3,5,5-trimethylhexanal, 2.5% by weight of 3,5,5-trimethylhexanol, 3.4% by weight of residual C8 hydrocarbons, and 0.6% by weight of high-boilers.

The reaction discharge was freed from rhodium catalyst by distillation on a laboratory distillation column.

The Rh-free hydroformylation discharge was then hydrogenated in the liquid phase in a fixed-bed reactor in the presence of a Cu/Cr/Ni catalyst at 180° C. and 25 bar. After hydrogenation of 3,5,5-trimethylhexanal to give the target product 3,5,5-trimethylhexanol, the hydrogenation discharge was freed from low-boilers (C8 hydrocarbons) by controlled distillation.

The distillation process gave a 3,5,5-trimethylhexanol of purity above 99.5% by weight.

Using a method similar to the procedure carried out under Example 1, 6 mol of the resultant 3,5,5-trimethylhexanol were reacted with 4 mol of benzoic acid and tetrabutyl titanate.

Distillation gave 3,5,5-trimethylhexyl benzoate at 99.7% purity as determined by gas chromatography.

The dynamic viscosity of the product at 20° C. was 7.9 mpa*s.

Example 4

Comparison of Volatilities of 2-ethylhexyl Benzoate, 3,5,5-trimethylhexyl Benzoate, and Isononyl Benzoate by Dynamic TGA Measurement In order to reach conclusions concerning the volatility of the products, the weight losses of the benzoic esters prepared in Examples 1 to 3 were compared by the dynamic TGA method.

To this end, about 40 mg of a specimen were heated under nitrogen in a DuPont Instrument TGA 951 device in the temperature range from 20 to 300° C., using a dynamic temperature rise of 10 K/min, and the respective weight loss in % was determined.

The table below lists the unevaporated proportions (=100%—weight loss in %):

TABLE 1

| Temperature in ° C. | Isononyl benzoate | 2-Ethylhexyl benzoate (Comparative Example) | 3,5,5-Trimethylhexyl benzoate (Comparative Example) |
|---|---|---|---|
| 140 | 98.5% | 98.1% | 93.6% |
| 170 | 93.7% | 91.1% | 72.9% |
| 200 | 75.7% | 68.2% | 9.4% |
| 230 | 24.2% | 12.4% | 0% |

The temperature at which 50% of the specimen has evaporated is 218° C. for the isononyl benzoate of the invention and only 213° C. for the comparative specimen 2-ethylhexyl benzoate. In the case of 3,5,5-trimethylhexyl benzoate, the temperature at which 50% of the specimen has evaporated is as low as 184° C.

This provides unambiguous confirmation of the lower volatility of the product prepared according to the invention in relation to the comparative products.

Example 5

Preparation of Plastisols

The fast-gelling plasticizers are represented on their own in mixing specifications 1 to 3, in order to expose more markedly the differences between these grades. Mixing specifications 4-6 comprise industrially relevant mixtures of VESTINOL 9 (DINP from OXENO Olefinchemie GmbH) with fast-fusers in typical wear layer formulations.

The weight used of the components is found in the table below.

TABLE 2

| Mixing specifications (all data in phr (=parts by weight per 100 parts of PVC)) | | | | | | |
|---|---|---|---|---|---|---|
| | 1 | 2 | 3 | 4 | 5 | 6 |
| VESTOLIT B 7021 (Emulsion PVC) | 100 | 100 | 100 | 100 | 100 | 100 |
| VESTINOL 9 (DINP, OXENO) | 0 | 0 | 0 | 35 | 35 | 35 |
| Isononyl benzoate (from Example 1) | 50 | | | 15 | | |
| 2-Ethylhexyl benzoate (from Example 2) | | 50 | | | 15 | |
| 3,5,5-trimethylhexyl benzoate (from Example 3) | | | 50 | | | 15 |
| Drapex 39 (Costabilizer, Crompton) | 3 | 3 | 3 | 3 | 3 | 3 |
| Mark CZ 140 (Ca/Zn Stab., Crompton) | 1.5 | 1.5 | 1.5 | 1.5 | 1.5 | 1.5 |

Prior to addition, the temperature of the plasticizers was controlled to 25° C. The liquid constituents were weighed into a PE beaker first, followed by the pulverulent constituents. The mixture was mixed by stirring with a paste spatula until all the powder had been wetted. The mixing beaker was then clamped into the clamping equipment of a dissolver mixer. Prior to immersing the stirrer into the mixture, the rotation rate was set at 1800 revolutions per minute. After the stirrer had been switched on stirring was continued until the temperature on the digital display of the temperature sensor reached 30.0° C. This ensured that homogenization of the plastisol was achieved with defined energy input. The temperature of the plastisol was then immediately controlled to 25.0° C.

Example 6

Measurement of Plastisol Viscosities

The viscosities of the plastisols prepared in Example 5 were measured as follows by a method based on DIN 53 019 using the Physica DSR 4000 rheometer which is controlled by US 200 software.

The plastisol was again stirred with a spatula in the feed vessel and tested in accordance with the operating instructions in test system Z3 (DIN 25 mm). Measurement proceeded automatically at 25° C. by way of the abovementioned software. The settings were as follows:

Pre-shear of 100 s$^{-1}$ for a period of 60 s, during which no values were measured, A downward progression beginning at 200 s$^{-1}$ and ending at 0.1 s$^{-1}$, divided into a logarithmic series with 30 steps, the duration for each point of measurement being 5 s.

After the test, the test data were processed automatically by the software. Viscosity was plotted as a function of shear rate. Each of the measurements was made after 2 h, 24 h, and 7 d. Between these junctures, the paste was stored at 25° C.

The two tables below list these viscosity values obtained after each of the storage times given, for shear rates of 1.06 s$^{-1}$ and 118 s$^{-1}$.

TABLE 3

Shear rate 1.06 s$^{-1}$ (viscosity data in Pa*s)

| Mixing specification | 1 | 2 | 3 | 4 | 5 | 6 |
|---|---|---|---|---|---|---|
| 2 h | 0.71 | 0.81 | 0.60 | 1.97 | 1.96 | 1.81 |
| 24 h | 0.93 | 1.24 | 0.77 | 2.35 | 2.41 | 2.39 |
| 7 d | 1.39 | 2.63 | 0.99 | 2.93 | 3.19 | 3.04 |

TABLE 4

Shear rate 118 s$^{-1}$ (viscosity data in Pa*s)

| Mixing specification | 1 | 2 | 3 | 4 | 5 | 6 |
|---|---|---|---|---|---|---|
| 2 h | 0.59 | 0.61 | 0.46 | 2.50 | 2.49 | 2.14 |
| 24 h | 0.73 | 0.86 | 0.57 | 2.91 | 2.93 | 2.93 |
| 7 d | 1.00 | 1.51 | 0.72 | 3.45 | 3.60 | 3.51 |

The measured values listed in Tables 3 and 4 are intended to show that the viscosity level of the plastisols using the isononyl benzoate of the invention differs only insignificantly from that of the two prior-art benzoates. In particular, the three benzoates differ very little in blends with DINP.

Example 7

Measurement of Gelling Properties

The gelling performance of the plastisols was tested in a Bohlin CVO oscillation viscometer (measurement system PP20), operated with shear stress control.

The following parameters were set:
Mode: temperature gradient
Start temperature: 25° C.
end temperature: 180° C.
heating/cooling rate: 2° C./min
temperature after measurement: 25° C.
oscillation frequency: 2 Hz
delay time: 1 s
waiting time: 15 s
continuous oscillation: on
automatic shear stress preset: on
shear stress at start: 0.3 Pa
required deformation: 0.002
gap width 0.5 mm Test Procedure:

A spatula was used to apply a drop of the plastisol to be tested (mixing specifications 1-3 from Example 5), free from air bubbles, to the lower plate of the test system. Care was taken here that some plastisol could exude uniformly out of the measurement system (not more than about 6 mm overall) after the measurement system has been closed. The protective covering, which also serves for thermal insulation, is then superimposed, and the test is started.

The "complex viscosity" of the plastisol was plotted as a function of temperature. The start of gelling is recognizable via a sudden marked rise in complex viscosity. The earlier the onset of this viscosity rise, the better the gelling capability of the system.

FIG. 1 plots that section of the viscosity/temperature curve ("gelation curve") relevant for the onset of gelation (see FIG. 1). The Y axis indicates complex viscosities in Pa.s, and the X axis indicates temperatures in ° C. The continuous line denotes plastisol 3 (3,5,5-trimethylhexyl benzoate) and the dotted line denotes plastisol 2 (2-ethylhexyl benzoate), while the dashed line denotes plastisol 1 (isononyl benzoate).

This presentation, which for simplicity only includes the formulations of the fast-gellers without DINP (1-3), shows that the onset of the marked rise in viscosity, i.e. the onset of gelation, is markedly earlier for the isononyl benzoate plastisol than for the corresponding plastisol using 3,5,5-trimethylhexyl benzoate. The somewhat lower gelling temperature for the plastisol based on 2-ethylhexyl benzoate is in agreement with the expectation that gelling temperature will fall with a reduction in chain length. It is surprising here that the effect of the different branching at the same molecular weight is considerably more significantly apparent here than the effect on moving from 2-ethylhexyl benzoate (C8) to isononyl benzoate (C9).

Example 8

Assessment of Low-temperature Properties Via Torsional Oscillation Analysis

The plastisols prepared in Example 5 were spread and gelled to give films of 1 mm thickness in a conventional laboratory gelling oven (Mathis LTSV) at 200° C. for 2 minutes.

Pieces of length 60 mm, width 80 mm, and thickness 1 mm were then stamped out from the films, and stiffness G' and loss modulus G" were determined for each of these at temperatures of from −100 to +100° C., at frequency 1 s$^{-1}$ in MYRENNE ATM III torsion pendulum equipment to DIN EN ISO 6721 (Part 2).

The glass transition temperature $T_G$ was determined from the maximum of G", and is a measure of flexibility at low temperatures.

The glass transition temperatures of the films produced from plastisols 1-6 from Example 5 can be seen in Table 5:

TABLE 5

| Plastisol No. | 1 | 2 | 3 | 4 | 5 | 6 |
|---|---|---|---|---|---|---|
| $T_G$ in °C. | −49 | −47 | −39 | −35 | −35 | −33 |

Whereas the glass transition temperatures achievable using isononyl benzoate and 2-ethylhexyl-benzoate, in particular in mixtures, are at a similar level, isononyl benzoate is markedly preferable to 3,5,5-trimethylhexyl benzoate.

In summary it can be stated that, while the viscosity level is practically identical, mixing specifications based on isononyl benzoate have marked advantages in relation to gelling capability, low-temperature flexibility, and volatility when compared with those based on 3,5,5-trimethylhexyl benzoate.

Particular factors arising from comparison with mixing specifications based on 2-ethylhexyl benzoate are a reduction in volatility and again an improvement in low-temperature flexibility.

The present application claims priority to German Patent Application 10217186.6-44 dated Apr. 18, 2002, which is hereby incorporated by reference in its entirety. Further, all references discussed above are hereby incorporated by reference in their entireties.

What is claimed is:

1. A mixture comprising isomeric isononyl benzoates, wherein an isononyl alcohol mixture obtained by saponifying the isomeric isononyl benzoates comprises a mixture of isomeric isononyl alcohols other than 3,5,5-trimethylhexanol and from 1 to less than 10 mol % of 3,5,5-trimethylhexanol.

2. A mixture comprising:
from 1 to 99% by weight of isomeric isononyl benzoates,
wherein an isononyl alcohol mixture obtained by saponifying the isomeric isononyl benzoates comprises a mixture of isomeric isononyl alcohols other than 3,5,5-trimethylhexanol, from 1 to less than 10 mol % of 3,5,5-trimethylhexanol, and from 1 to 99% by weight of a dialkyl phthalate,
wherein at least one of the alkyl radicals of the dialkyl phthalate is an alkyl radical having from 4 to 13 carbon atoms.

3. The mixture according to claim 2, wherein the mixture comprises at least one diisononyl phthalate.

4. The mixture according to claim 3, wherein an isononyl alcohol mixture is obtained by saponifying the isomeric diisononyl phthalates, wherein the mixture comprises a mixture of isomeric isononyl alcohols other than 3,5,5-trimethylhexanol and from 1 to less than 10 mol % of 3,5,5-trimethylhexanol.

5. A mixture comprising:
from 1 to 99% by weight of isomeric isononyl benzoates,
wherein an isononyl alcohol mixture obtained by saponifying the isomeric isononyl benzoates comprises less than 10 mol % of 3,5,5 trimethylhexanol; and from 1 to 99% by weight of at least one alkyl adipate,
wherein at least one of the alkyl radicals of which is an alkyl radical having from 4 to 13 carbon atoms.

6. The mixture according to claim 5, wherein the mixture comprises an isomeric diisononyl adipate.

7. The mixture according to claim 6, wherein the isononyl alcohol mixture obtained by saponifying the isomeric diisononyl adipates comprises less than 10 mol % of 3,5,5-trimethylhexanol.

8. A mixture comprising:
from 1 to 99% by weight of isomeric isononyl benzoates,
wherein an isononyl alcohol mixture obtained by saponifying the isomeric isononyl benzoates comprises less than 10 mol % of 3,5,5-trimethylhexanol; and from 1 to 99% by weight of alkyl cyclohexanedicarboxylate,
wherein at least one of the alkyl radicals of which is an alkyl radical having from 4 to 13 carbon atoms.

9. The mixture according to claim 8, wherein the alkyl cyclohexanedicarboxylate is at least in part an isomeric diisononyl cyclohexanedicarboxylate.

10. The mixture according to claim 9, wherein an isononyl alcohol mixture obtained by saponifying the diisononyl cyclohexanedicarboxylate comprises less than 10 mol % of 3,5,5-trimethylhexanol.

11. A process for preparing isomeric isononyl benzoates comprising:
esterifying benzoic acid having the formula $C_6H_5COOH$ with a mixture of isomeric nonyl alcohols,
wherein the mixture comprises a mixture of isomeric isononyl alcohols other than 3,5,5-trimethylhexanol and from 1 to less than 10 mol % of 3,5,5-trimethylhexanol.

12. A process for preparing isomeric nonyl benzoates comprising:
transesterifying an alkyl benzoate with a mixture of nonyl alcohols comprising a mixture of isomeric isononyl alcohols other than 3,5,5-trimethylehexanol and less than 10 mol % of 3,5,5-trimethylhexanol.

13. A method, comprising:
contacting the mixture according to claim 1 with a plastic.

14. The method according to claim 13, wherein the plastic is PVC.

15. A method, comprising:
contacting the mixture according to claim 2 with a plastic.

16. The method according to claim 15, wherein the plastic is PVC.

17. A method, comprising:
contacting the mixture according to claim 5 with a plastic.

18. The method according to claim 17, wherein the plastic is PVC.

19. A method, comprising:
contacting the mixture according to claim 8 with a plastic.

20. The method according to claim 19, wherein the plastic is PVC.

21. A plastisol, comprising:
the mixture according to claim 1 and PVC.

22. A plastisol, comprising:
the mixture according to claim 2 and PVC.

23. A plastisol, comprising:
the mixture according to claim 5 and PVC.

24. A plastisol, comprising:
the mixture according to claim 8 and PVC.

25. A synthetic leather, flooring, cushion vinyl flooring, or wallpaper, comprising:
the mixture according to claim 1, a plastic, and at least one member selected from the group consisting of a filler, pigment, stabilizer, lubricant, blowing agent, kicker, antioxidant, and biocide.

26. A method of making a synthetic leather, flooring, cushion vinyl flooring, or wallpaper, comprising:
contacting the mixture according to claim 1 with a plastic and at least one member selected from the group consisting of a filler, pigment, stabilizer, lubricant, blowing agent, kicker, antioxidant, and biocide.

27. A paint, ink, or coating, comprising:
the mixture according to claim 1, a plastic, and at least one member selected from the group consisting of a filler, pigment, stabilizer, lubricant, antioxidant, and biocide.

28. A method of making an adhesive or component of an adhesive, comprising:
contacting the mixture according to claim 1 with a plastic and at least one member selected from the group consisting of a filler, pigment, stabilizer, lubricant, blowing agent, kicker, antioxidant, and biocide.

29. A synthetic leather, flooring, cushion vinyl flooring, or wallpaper, comprising:
the mixture according to claim 2, a plastic, and at least one member selected from the group consisting of a filler, pigment, stabilizer, lubricant, blowing agent, kicker, antioxidant, and biocide.

30. A method of making a synthetic leather, flooring, cushion vinyl flooring, or wallpaper, comprising:
contacting the mixture according to claim 2 with a plastic and at least one member selected from the group consisting of a filler, pigment, stabilizer, lubricant, blowing agent, kicker, antioxidant, and biocide.

31. A paint, ink, or coating, comprising:
the mixture according to claim 2, a plastic, and at least one member selected from the group consisting of a filler, pigment, stabilizer, lubricant, antioxidant, and biocide.

32. A method of making an adhesive or component of an adhesive, comprising:
contacting the mixture according to claim 2 with a plastic and at least one member selected from the group consisting of a filler, pigment, stabilizer, lubricant, blowing agent, kicker, antioxidant, and biocide.

33. A synthetic leather, flooring, cushion vinyl flooring, or wallpaper, comprising:
the mixture according to claim 5, a plastic, and at least one member selected from the group consisting of a filler, pigment, stabilizer, lubricant, blowing agent, kicker, antioxidant, and biocide.

34. A method of making a synthetic leather, flooring, cushion vinyl flooring, or wallpaper, comprising:
contacting the mixture according to claim 5 with a plastic and at least one member selected from the group consisting of a filler, pigment, stabilizer, lubricant, blowing agent, kicker, antioxidant, and biocide.

35. A paint, ink, or coating, comprising:
the mixture according to claim 5, a plastic, and at least one member selected from the group consisting of a filler, pigment, stabilizer, lubricant, antioxidant, and biocide.

36. A method of making an adhesive or component of an adhesive, comprising:
contacting the mixture according to claim 5 with a plastic and at least one member selected from the group consisting of a filler, pigment, stabilizer, lubricant, blowing agent, kicker, antioxidant, and biocide.

37. A synthetic leather, flooring, cushion vinyl flooring, or wallpaper, comprising:
the mixture according to claim 8, a plastic, and at least one member selected from the group consisting of a filler, pigment, stabilizer, lubricant, blowing agent, kicker, antioxidant, and biocide.

38. A method of making a synthetic leather, flooring, cushion vinyl flooring, or wallpaper, comprising:
contacting the mixture according to claim 8 with a plastic and at least one member selected from the group consisting of a filler, pigment, stabilizer, lubricant, blowing agent, kicker, antioxidant, and biocide.

39. A paint, ink, or coating, comprising:
the mixture according to claim 8, a plastic, and at least one member selected from the group consisting of a filler, pigment, stabilizer, lubricant, antioxidant, and biocide.

40. A method of making an adhesive or component of an adhesive, comprising:
contacting the mixture according to claim 8 with a plastic and at least one member selected from the group consisting of a filler, pigment, stabilizer, lubricant, blowing agent, kicker, antioxidant, and biocide.

41. The mixture according to claim 5, wherein the isononyl alcohol mixture comprises from 1 to less than 10 mol % of 3,5,5-trimethylhexanol.

42. The mixture according to claim 8, wherein the isononyl alcohol mixture comprises from 1 to less than 10 mol % of 3,5,5-trimethylliexanol.

43. The process as claimed in claim 12, wherein the mixture of isomeric isononyl alcohols comprises from 1 to less than 10 mol % of 3,5,5-trimethylhexanol.

* * * * *